US010448975B2

United States Patent
Potash et al.

(10) Patent No.: US 10,448,975 B2
(45) Date of Patent: *Oct. 22, 2019

(54) MULTI-AXIAL SPINAL FIXATION SYSTEM

(71) Applicant: SPINE WAVE, INC., Shelton, CT (US)

(72) Inventors: Robert Potash, Seymour, CT (US);
Anthony James, Bartlett, TN (US)

(73) Assignee: SPINE WAVE, INC., Shelton, CT (US)

( * ) Notice: Subject to any disclaimer, the term of this patent is extended or adjusted under 35 U.S.C. 154(b) by 7 days.

This patent is subject to a terminal disclaimer.

(21) Appl. No.: 15/864,165

(22) Filed: Jan. 8, 2018

(65) Prior Publication Data
US 2018/0125536 A1 May 10, 2018

Related U.S. Application Data

(60) Continuation of application No. 14/984,154, filed on Dec. 30, 2015, now Pat. No. 9,861,395, which is a
(Continued)

(51) Int. Cl.
*A61B 17/70* (2006.01)
*B25B 23/10* (2006.01)
(Continued)

(52) U.S. Cl.
CPC ...... *A61B 17/7037* (2013.01); *A61B 17/7002* (2013.01); *A61B 17/7032* (2013.01);
(Continued)

(58) Field of Classification Search
CPC ............ A61B 17/7035; A61B 17/7037; A61B 17/8685; A61B 17/7032; A61B 17/7002
See application file for complete search history.

(56) References Cited

U.S. PATENT DOCUMENTS 717,024 A 12/1902 Nellenbogen
2,190,585 A 2/1940 Rhinevault
(Continued)

FOREIGN PATENT DOCUMENTS

| DE | 19512709 A1 | 10/1996 |
| EP | 1174092 A2 | 1/2002 |
| EP | 1269929 A1 | 1/2003 |
| FR | 2624720 | 6/1989 |
| FR | 2867375 A1 | 9/2005 |

OTHER PUBLICATIONS

WCL Company; "Spring Washers, Descriptions and Design Considerations"; Copyright 2005-2006; http://www.wclco.com/Sping_Washers/Descriptions.php; Dates Sep. 1, 2011 (g pgs).
Office Action Summary issued in U.S. Appl. No. 12/196,661 dated Aug. 31, 2012; (22 pgs).
PCT Search Report and Opinion for PCT/US2007/084492 (related international application), dated May 22, 2008, pp. 4, 7-11.

*Primary Examiner* — Lynnsy M Summitt
*Assistant Examiner* — Tara Rose E Carter
(74) *Attorney, Agent, or Firm* — Hoffman & Baron, LLP

(57) ABSTRACT

A spinal fixation system includes a rod and anchor devices that include a bone engaging fastener having a head defining a spherical socket. A ball insert is placed within the socket and rotated so that the ball insert is juxtaposed with the socket. The anchor device further includes a yoke defining a yoke channel for receiving the rod and a stem engaged to the ball insert captured within the socket. A sleeve disposed between the yoke channel and the fastener head supports the rod. A set screw is operable to clamp the rod against the sleeve and draw the insert into engagement within the socket. A releasable detent defined between the yoke and the fastener head is configured to releasably retain the yoke in at least one discrete position relative to the fastener. Portions of the releasable detent may also exert a frictional retention force against the fastener head.

12 Claims, 14 Drawing Sheets

Related U.S. Application Data division of application No. 13/925,992, filed on Jun. 25, 2013, now Pat. No. 9,226,777, which is a continuation of application No. 11/762,898, filed on Jun. 14, 2007, now Pat. No. 8,475,500, which is a continuation-in-part of application No. 11/560,587, filed on Nov. 16, 2006, now Pat. No. 8,162,990.

(51) Int. Cl.
*A61B 17/88* (2006.01)
*A61B 17/86* (2006.01)

(52) U.S. Cl.
CPC ...... *A61B 17/7082* (2013.01); *A61B 17/7086* (2013.01); *A61B 17/8605* (2013.01); *A61B 17/8685* (2013.01); *A61B 17/88* (2013.01); *B25B 23/105* (2013.01); *A61B 17/8875* (2013.01)

(56) References Cited

U.S. PATENT DOCUMENTS

| | | | |
|---|---|---|---|
| 4,241,463 A | 12/1980 | Khovaylo | |
| 4,763,644 A | 8/1988 | Webb | |
| 4,805,602 A | 2/1989 | Puno et al. | |
| 4,936,855 A | 6/1990 | Sherman | |
| 4,946,458 A | 8/1990 | Harms et al. | |
| 5,129,388 A | 7/1992 | Vignaud et al. | |
| 5,207,678 A | 5/1993 | Harms et al. | |
| 5,217,497 A | 6/1993 | Mehdian | |
| 5,257,993 A | 11/1993 | Asher et al. | |
| 5,346,493 A | 9/1994 | Stahurski et al. | |
| 5,354,299 A | 10/1994 | Coleman | |
| 5,360,431 A | 11/1994 | Puno et al. | |
| 5,437,669 A | 8/1995 | Yuan et al. | |
| 5,443,467 A | 8/1995 | Biedermann et al. | |
| 5,443,476 A | 8/1995 | Shapiro | |
| 5,466,237 A | 11/1995 | Byrd, III et al. | |
| 5,474,555 A | 12/1995 | Puno et al. | |
| 5,476,464 A | 12/1995 | Metz-Stavenhagen et al. | |
| 5,501,684 A | 3/1996 | Schlapfer et al. | |
| 5,536,268 A | 7/1996 | Griss | |
| 5,549,608 A | 8/1996 | Errico et al. | |
| 5,562,737 A | 10/1996 | Graf | |
| 5,584,834 A | 12/1996 | Errico et al. | |
| 5,586,984 A | 12/1996 | Errico et al. | |
| 5,591,166 A | 1/1997 | Bernhardt et al. | |
| 5,628,740 A | 5/1997 | Mullane | |
| 5,647,873 A | 7/1997 | Errico et al. | |
| 5,667,508 A | 9/1997 | Errico et al. | |
| 5,716,356 A | 2/1998 | Biedermann et al. | |
| 5,733,285 A | 3/1998 | Errico et al. | |
| 5,733,286 A * | 3/1998 | Errico ................ A61B 17/7037 606/266 | |
| 5,735,851 A | 4/1998 | Errico et al. | |
| 5,752,957 A | 5/1998 | Ralph et al. | |
| 5,797,911 A | 8/1998 | Sherman et al. | |
| 5,800,435 A | 9/1998 | Errico et al. | |
| 5,876,403 A | 3/1999 | Shitoto | |
| 5,879,350 A | 3/1999 | Sherman et al. | |
| 5,885,286 A | 3/1999 | Sherman et al. | |
| 6,050,997 A | 4/2000 | Mullane | |
| 6,146,383 A | 11/2000 | Studer et al. | |
| 6,248,107 B1 | 6/2001 | Foley et al. | |
| 6,267,765 B1 | 7/2001 | Taylor et al. | |
| 6,309,391 B1 | 10/2001 | Crandall et al. | |
| 6,352,537 B1 | 3/2002 | Strnad | |
| 6,402,752 B2 | 6/2002 | Schaffler-Wachter et al. | |
| 6,451,021 B1 | 9/2002 | Ralph et al. | |
| 6,537,276 B2 | 3/2003 | Metz-Stavenhagen | |
| 6,540,748 B2 | 4/2003 | Lombardo | |
| 6,554,834 B1 | 4/2003 | Crozet et al. | |
| 6,565,565 B1 | 5/2003 | Yuan et al. | |
| 6,585,737 B1 | 7/2003 | Baccelli et al. | |
| 6,623,485 B2 | 9/2003 | Doubler et al. | |
| 6,626,908 B2 | 9/2003 | Cooper et al. | |
| 6,660,004 B2 | 12/2003 | Barker et al. | |
| 6,660,005 B2 | 12/2003 | Toyama et al. | |
| 6,695,843 B2 | 2/2004 | Biedermann et al. | |
| 6,802,844 B2 | 10/2004 | Ferree | |
| 6,835,196 B2 | 12/2004 | Biedermann et al. | |
| 6,887,242 B2 | 5/2005 | Doubler et al. | |
| 7,066,937 B2 | 6/2006 | Shluzas | |
| 7,081,116 B1 | 7/2006 | Carly | |
| 7,081,117 B2 | 7/2006 | Bono et al. | |
| 7,087,057 B2 | 8/2006 | Konieczynski et al. | |
| 7,144,396 B2 | 12/2006 | Shluzas | |
| 7,625,396 B2 | 12/2009 | Jackson | |
| 7,776,067 B2 | 8/2010 | Jackson | |
| 7,819,899 B2 | 10/2010 | Lancial | |
| 7,833,250 B2 | 11/2010 | Jackson | |
| 7,875,060 B2 | 1/2011 | Chin | |
| 8,162,988 B2 | 4/2012 | Delecrin et al. | |
| 8,414,622 B2 | 4/2013 | Potash | |
| 8,956,362 B2 | 2/2015 | Landry et al. | |
| 2001/0001119 A1 | 5/2001 | Lombardo | |
| 2003/0004512 A1 | 1/2003 | Farris et al. | |
| 2003/0073997 A1 | 4/2003 | Doubler et al. | |
| 2003/0100897 A1 | 5/2003 | Metz-Stavenhagen | |
| 2003/0153911 A1 | 8/2003 | Shluzas | |
| 2003/0163133 A1 | 8/2003 | Altarac et al. | |
| 2003/0185621 A1 | 10/2003 | Rundle et al. | |
| 2004/0054371 A1 | 3/2004 | Dierks et al. | |
| 2004/0097933 A1 | 5/2004 | Lourdel et al. | |
| 2004/0138662 A1 | 7/2004 | Landry et al. | |
| 2004/0215190 A1 | 10/2004 | Nguyen et al. | |
| 2004/0260284 A1 | 12/2004 | Parker | |
| 2005/0013658 A1 | 1/2005 | Muders et al. | |
| 2005/0070899 A1 | 3/2005 | Doubler et al. | |
| 2005/0070901 A1 | 3/2005 | David | |
| 2005/0137594 A1 | 6/2005 | Doubler et al. | |
| 2005/0149031 A1 | 7/2005 | Ciccone et al. | |
| 2005/0192571 A1 * | 9/2005 | Abdelgany ........ A61B 17/7037 411/427 | |
| 2005/0192572 A1 | 9/2005 | Abdelgany | |
| 2005/0192573 A1 * | 9/2005 | Abdelgany ........ A61B 17/7037 606/276 | |
| 2005/0203516 A1 * | 9/2005 | Biedermann ........ A61B 17/701 606/267 | |
| 2005/0216003 A1 | 9/2005 | Biedermann et al. | |
| 2005/0267472 A1 | 12/2005 | Bidermann et al. | |
| 2005/0277931 A1 | 12/2005 | Sweeney et al. | |
| 2006/0036242 A1 | 2/2006 | Nilsson et al. | |
| 2006/0036252 A1 | 2/2006 | Baynham et al. | |
| 2006/0167455 A1 | 2/2006 | Clement et al. | |
| 2006/0052783 A1 | 3/2006 | Dant et al. | |
| 2006/0052784 A1 | 3/2006 | Dant et al. | |
| 2006/0052786 A1 | 3/2006 | Dant et al. | |
| 2006/0100621 A1 | 5/2006 | Jackson | |
| 2006/0129149 A1 | 6/2006 | Iott et al. | |
| 2006/0149232 A1 | 7/2006 | Sasing | |
| 2006/0149240 A1 | 7/2006 | Jackson | |
| 2006/0212034 A1 | 9/2006 | Tripplett et al. | |
| 2006/0276789 A1 | 12/2006 | Jackson | |
| 2007/0032849 A1 | 2/2007 | Schlapfer et al. | |
| 2007/0093832 A1 | 4/2007 | Abdelgany | |
| 2007/0118123 A1 | 5/2007 | Strausbaugh et al. | |
| 2007/0173817 A1 | 7/2007 | Sournac et al. | |
| 2007/0198014 A1 | 8/2007 | Graf et al. | |
| 2008/0003054 A1 | 1/2008 | Fan | |
| 2008/0119857 A1 | 5/2008 | Potash et al. | |
| 2008/0119858 A1 | 5/2008 | Potash | |
| 2008/0262556 A1 | 10/2008 | Jacofsky et al. | |
| 2008/0312692 A1 | 12/2008 | Brennan et al. | |
| 2009/0118772 A1 | 5/2009 | Diederich et al. | |
| 2009/0264896 A1 | 10/2009 | Biedermann et al. | |
| 2010/0222822 A1 | 9/2010 | Farris et al. | |

* cited by examiner

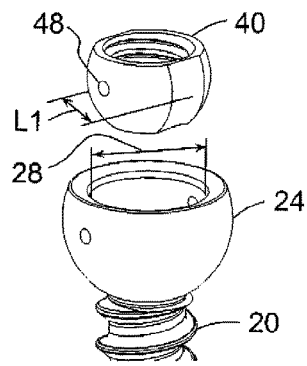
FIG. 8a
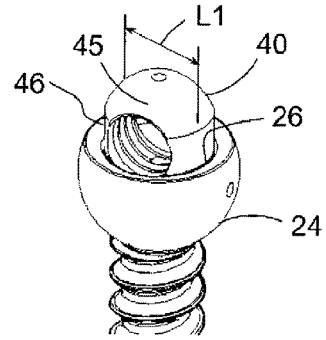
FIG. 8b
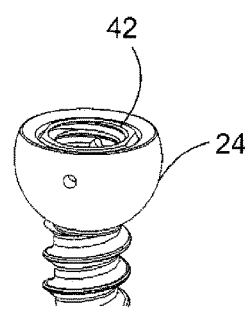
FIG. 8c
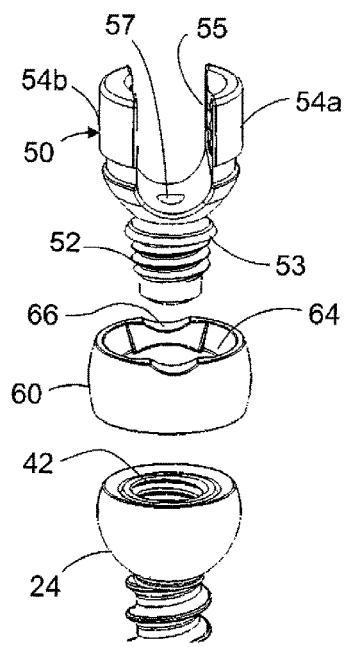
FIG. 8d
FIG. 8e
FIG. 8f

MULTI-AXIAL SPINAL FIXATION SYSTEM

CROSS-REFERENCES TO RELATED APPLICATIONS

This application is a continuation application of application Ser. No. 14/984,154, filed on Dec. 30, 2015, now U.S. Pat. No. 9,861,395, which is a divisional application of application Ser. No. 13/925,992, filed on Jun. 25, 2013, now U.S. Pat. No. 9,226,777, which is a continuation application of application Ser. No. 11/762,898, filed on Jun. 14, 2007, now U.S. Pat. No. 8,475,500, which is a continuation-in-part application of application Ser. No. 11/560,587, filed on Nov. 16, 2006, now U.S. Pat. No. 8,162,990, which issued on Apr. 24, 2012, which are each herein incorporated by reference in its entirety.

BACKGROUND

The present invention relates to spinal fixation systems and particularly to an anchor device that incorporates multi-axial fixation to the spine.

Several techniques and systems have been developed for correcting and stabilizing injuries to or malformation of the spine. In one type of system, an elongated member such as a bendable rod is disposed longitudinally along a length of the spine, spanning two or more vertebral levels. In certain applications, the rod is bent to correspond to the normal curvature of the spine in the particular region being instrumented, such as the normal kyphotic curvature of the thoracic region or the lordotic curvature of the lumbar region. In accordance with such a system, the rod is engaged to various vertebrae along a length of the spinal column by way of a number of anchor devices that utilize a variety of fixation elements configured to engage specific portions of the vertebra and other bones. For instance, one such fixation element is a hook that is configured to engage the laminae of the vertebra. Another very prevalent fixation element is a screw that can be threaded into various parts of the vertebrae or other bones.

Early rod-type spinal fixation systems incorporated anchor devices that permitted very limited relative orientations of the rod relative to the fixation element. As these system evolved, various degrees of freedom of relative orientation were integrated into the system. For instance, in one system a bone screw may be engaged to the spinal rod at a range of planar angles. This so-called variable angle screw allows pivoting of the bone screw in a single plane parallel to the plane of the spinal rod. One goal achieved by the variable angle screw is that the surgeon can apply vertebral fixation elements to the spine in more appropriate anatomic positions.

Another rod-type fixation system utilizes fixation elements having a body that defines a slot within which the spinal rod is received. The slot includes a threaded bore into which a threaded plug is engaged to secure the rod within the body of the fixation element. One benefit of this type of fixation element is that the fixation element may be positioned directly beneath the elongated rod, thereby reducing the overall bulkiness of the implant construct and minimizing trauma to the surrounding tissue.

On the other hand, these so-called "open back" fixation elements are capable only of pivoting about the spinal rod to achieve variable angular positions relative to the rod. While this limited range of relative angular positioning is acceptable for many spinal pathologies, many other cases require more creative orientation of a bone fastener relative to a spinal rod. Certain aspects of this problem are addressed by some prior multi-axial or poly-axial screws that are capable of various three-dimensional orientations with respect to the spinal rod. One type of poly-axial screw design, shown in U.S. Pat. No. 6,537,276 to Metz-Stavenhagen et al., includes a spherical projection on the top of the bone screw. An internally threaded receiver member pivotally supports the bone screw and a spinal rod on top of the spherical projection. An inner set screw is tightened into the receiver member to press the spinal rod against the spherical projection to accommodate various angular orientations of the bone screw relative to the rod. A similar multi-axial screw is disclosed in U.S. Pat. No. 5,466,237 to Byrd et al., except an outer nut is provided to secure the rod against the head of the bone screw.

In another approach shown in U.S. Pat. No. 4,946,458 to Harms et al., a spherical headed bone screw is supported within separate halves of a receiver member. The bottom of the halves are held together by a retaining ring. The top of the receiver halves are compressed about the bone screw by nuts threaded onto a threaded spinal rod. One detriment of this system is that the spinal rod must be threaded in order to accept the compression nuts, which has a tendency to weaken the spinal rod in the face of severe spinal loads. Harms et al. also describes in U.S. Pat. No. 5,207,678 another multi-axial pedicle screw wherein a compression member is provided between the rod and the head of the screw to exert a force on the screw head to lock the screw against the inner spherical surface of the receiver member.

Yet another approach is illustrated in U.S. Pat. No. 5,797,911 to Sherman et al., in which a U-shaped holder is provided that receives a bone fastener topped with a crown member. The holder accommodates a rod in a channel above the crown member and a compression member above the rod. The compression member presses on the rod and crown member to lock the fastener against the holder in any of a number of angles in three dimensions with respect to the rod. Another system shown in U.S. Pat. No. 5,733,285 to Errico et al., includes a holder having a tapered and colleted portion into which a bone fastener head is inserted. A sleeve is provided that translates down around the colleted portion to crush lock the colleted portion around the head of the bone fastener. This apparatus is bulky and difficult to manipulate given the external sliding locking mechanism. It is further dependent on the fit of the external sleeve and the relative strength of the collet and its bending and crushing portions for secure locking of the bone fastener head.

There is thus a need for a multi-axial or poly-axial fastener for use with a spinal fixation system that is simple to construct yet strong enough to withstand harsh spinal loads. This need should also be fulfilled by an anchor device that avoids the bulkiness of prior systems but can still achieve a simple and easy fixation of the spinal rod to the bone fastener mounted within the spine.

SUMMARY OF THE INVENTION

The present invention contemplates a spinal fixation system that incorporates multi-axial fixation characteristics in a low-profile, easy to construct anchor device. The system includes an elongated member, such as a spinal rod, that extends between spinal segments. A series of anchor devices anchor the rod to the spinal segments, with at least some of the anchor devices providing multi-axial fixation. In one embodiment of the invention, the multi-axial anchor device includes a bone engaging fastener that is adapted to engage a portion of the spine. In one specific embodiment, the fastener is a bone screw adapted to be threaded into the pedicle of a vertebra.

The head of the bone engaging fastener is provided with a spherical socket facing the spinal rod. A ball insert element is provided that incorporates a spherical surface for variable angular interface with the socket. The ball insert is further configured so that the insert may be introduced into the socket and then rotated within the socket so that the spherical surface is juxtaposed to the socket for captive retention therein.

In one configuration, the socket has an interior diameter and a smaller diametrical opening communicating therewith. The ball insert is configured as a truncated sphere having a spherical diameter slightly less than the interior diameter of the socket. A portion of the ball insert is formed to have an outer curved surface defining a cylinder having a maximum diameter less than the spherical diameter of the ball insert and less than the diameter of the socket opening. The ball insert is introduced into the socket by aligning the cylindrical diameter with the diameter of the opening and then placing the insert into the socket. The insert is thereafter rotated in the socket to juxtapose the spherical surface of the insert with the interior diameter of the socket to captively retain the insert.

Connection to the spinal rod is provided by way of a yoke that is engaged to the ball insert. In one embodiment, this engagement is accomplished by a threaded bore in the ball insert and a mating threaded stem of the yoke. The ball insert is free to swivel in the fastener socket and since the yoke is attached to the ball insert it is thereby also free to move in a multi-axial manner. The yoke defines a channel between opposing arms of the yoke, with the channel configured to snugly seat the rod therein.

A sleeve is provided that fits about an upper portion of the head of the bone engaging fastener. This upper portion provides a spherical surface to interface with a spherical lower cavity of the sleeve so that the sleeve may adapt a range of spherical angles relative to the bone engaging fastener as necessary to accommodate the position of the spinal rod relative thereto. The sleeve includes in one configuration opposing notches to receive and support the rod.

While the yoke does not itself support the spinal rod, it does support a set screw that is used to clamp the spinal rod to the notches in the sleeve. In one embodiment, the set screw is carried by a cap that fits over and around the arms of the yoke. The set screw is configured to engage internal threads defined in the yoke arms so that as the set screw is driven into the yoke a lower face of the screw contacts the spinal rod to drive it into the sleeve. In one embodiment, the set screw is supported within the cap so that the screw may rotate independently of the cap. The cap and the set screw may each define opposing grooves for mutually carrying a retaining ring used to fix the set screw against axial movement relative to the cap. The retaining ring does permit relative rotation so the set screw may be used to clamp the spinal rod.

The angular orientation of the yoke is adjusted relative to the bone engaging fastener to accommodate the position of the spinal rod relative to the portion of the spine. In one feature of the invention, this angular orientation is fixed by pressure engagement between the ball insert and the spherical socket of the head of the bone fastener. Thus, in accordance with this feature, the present invention contemplates that the set screw not only operates to firmly clamp the spinal rod within the yoke and against the sleeve, it also generates an array of forces that press the ball insert into the spherical socket. In particular, as the set screw is tightened within the threaded arms of the yoke, the pressure face of the set screw first contacts the spinal rod. As the set screw is advanced further into the yoke, the pressure face clamps the rod against the sleeve. At this point, the rod is generally firmly fixed to the yoke, although the yoke itself is not yet firmly fixed to the bone engaging fastener.

As the set screw is tightened further into the internal threads of the yoke arms, a reaction force is generated against the yoke itself, since the set screw cannot be driven any further into the rod of lower sleeve. This reaction force pulls the yoke upward, which in turn pulls the ball insert upward due to the threaded engagement between the ball insert and the threaded stem of the yoke. As the yoke and ball insert are pulled upward, the ball insert is pressed into the upper portion of the spherical socket of the head of the bone screw, thereby clamping the ball insert relative to the bone screw. With the ball insert clamped, further tightening of the set screw pushes against the rod to drive the sleeve into firm locking engagement with the spherical outer surface of the head of the bone fastener.

In a further aspect of the invention, a releasable detent is disposed between the yoke and the head of the fastener. The releasable detent is configured to releasably retain the yoke in at least one pre-determined position relative to the fastener. In one specific embodiment, the releasable detent is arranged so that the yoke is maintained in axial alignment with the threaded shank of the bone screw as it is driven into the spinal bone.

The releasable detent may include a cavity defined within the stem of the yoke and a spring and a retention ball seated within the cavity. The spring pushes the retention ball outward into contact with spherical surface of the socket in the fastener head. The socket may be provided with a dimple in axial alignment with the threaded shank of the bone screw to establish the pre-determined position for axial alignment of the yoke.

The releasable detent may also be configured to provide frictional movement of the yoke relative to the fastener such that the yoke is frictionally maintained in a position relative to the fastener other than the discrete position. In this aspect, the frictional force exerted by the releasable detent is sufficient to temporarily hold the yoke in any angular orientation relative to the bone screw. This feature allows for pre-positioning of the rod-receiving channel of the yoke while the spinal rod is being prepared for engagement with the fixation assembly, such as by bending the rod accordingly.

One benefit of the present invention is that it provides for solid anchoring between a spinal rod and a bone engaging fastener at variable spherical angles. A further benefit is that a common clamping element is provided to clamp the spinal rod and fix the angular position of the anchor device.

Yet another benefit resides in one aspect of the anchor device that reduces the overall prominence and profile of the components of the device. A still further benefit is that the relative angular position of the components may be temporarily held during implantation or in anticipation of engagement with a prepared spinal rod. Other benefits of the invention can be discerned from the following written description and accompanying figures.

DESCRIPTION OF THE FIGURES

FIGS. 8a-8f are side perspective views of a sequence of assembly of the components of the anchor device shown in FIG. 2.

DESCRIPTION OF THE PREFERRED EMBODIMENTS

Figure 1:
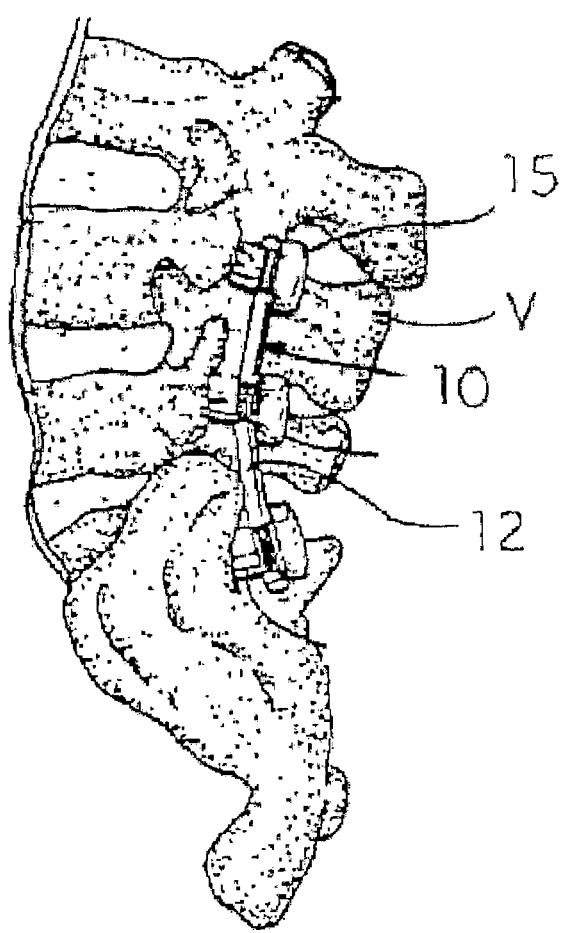
FIG. 1 is a transverse view of a portion of a spine with a fixation system utilizing an elongated members engaged between successive vertebrae.
Figure 3:
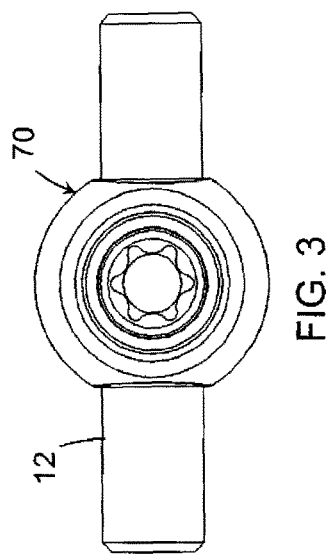
FIG. 3 is a top plan view of the anchor device shown in FIG. 2.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
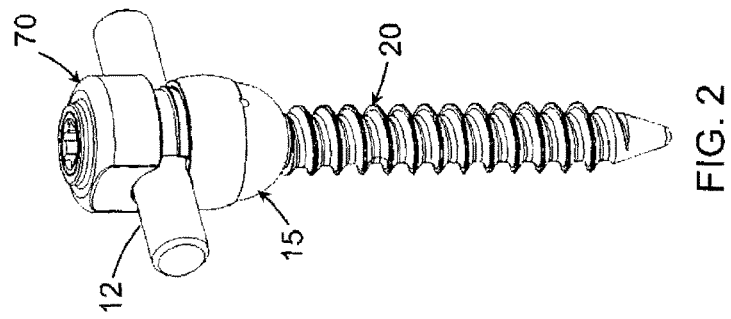
FIG. 2 is a side perspective view of an anchor device according to one embodiment of the invention for use in the fixation system shown in FIG. 1.

The present invention contemplates a spinal fixation system, such as the system 10 depicted in FIG. 1. As is known in the art, the fixation system 10 spans between successive vertebrae of the spine. An elongated member, such as rod 12, extends along the length of the spine and provides an anchor point for connecting each vertebra to the rod. The rod is typically contoured to approximate the normal curvature of the spine for the particular instrumented spinal segments. Anchor devices 15 are provided for connecting the vertebral segments to the rod. These anchor devices may include hooks, bolts, screws or other means for engaging a vertebra. For the purposes of the present discussion, the anchor device 15 includes a bone engaging fastener 20 which is a bone screw, as shown in FIG. 2. The bone screw 20 includes a threaded shank 22 configured for threaded engagement within a portion of a vertebra. In a specific example, the shank is configured for engagement within the pedicle of a vertebra.

Figure 5:
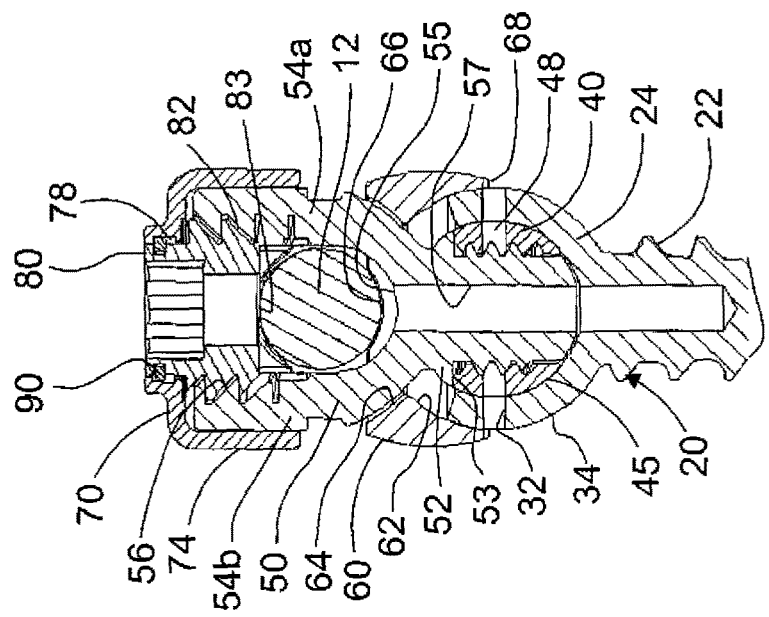
FIG. 5 is a longitudinal cross-sectional view of the anchor device illustrated in FIG. 2 along the longitudinal axis of the elongated member.
Figure 4:
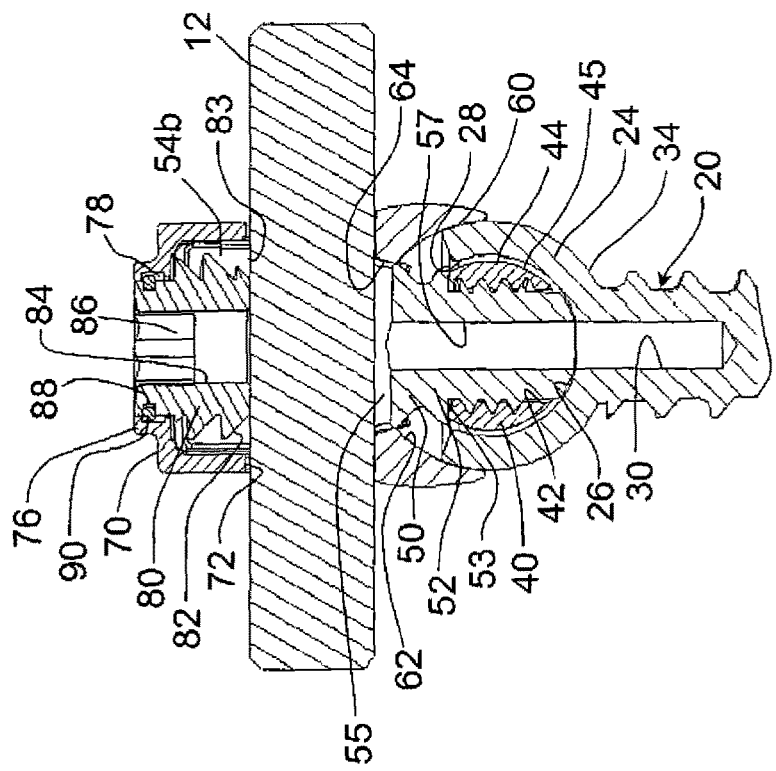
FIG. 4 is a side cross-sectional view of the anchor device of FIG. 2.

The bone engaging fastener or screw 20 further includes a head 24 by which the screw, and ultimately the vertebra, is anchored to the spinal rod 12. In accordance with one feature of the present invention, the head 24 defines a spherical socket 26 with a socket opening 28 facing the rod, as shown in FIGS. 4-5. The bone screw 20 further defines a central bore 30 intersecting the socket and extending part way into the threaded shank 22. A transverse bore 32 extends through the head 24 and across the socket, as best seen in FIG. 5. The function of the bores 30 and 32 are discussed herein. The head 24 includes a spherical outer surface 34.

It can be appreciated from considering FIGS. 4-5 that the spherical head 24 of the bone screw is more than simply hemi-spherical. In other words, the spherical socket 28 subtends a spherical angle of greater than 180° so that socket opening 28 is defined at a chord of the spherical socket. The planar diameter of the opening 28 at the chord is less than the inner diameter of the socket. In a specific embodiment, the spherical head subtends a spherical angle of about 240° and the planar chordal diameter of the socket opening 28 is about 90% the spherical diameter of the socket. It can thus be appreciated that a ball element of about the same spherical diameter disposed within the socket will be retained within the socket, unable to pass through the socket opening. It will be appreciated from the following discussion that a smaller planar chordal diameter will reduce the range of angulation of the articulating components of the anchor device.

Figure 6:
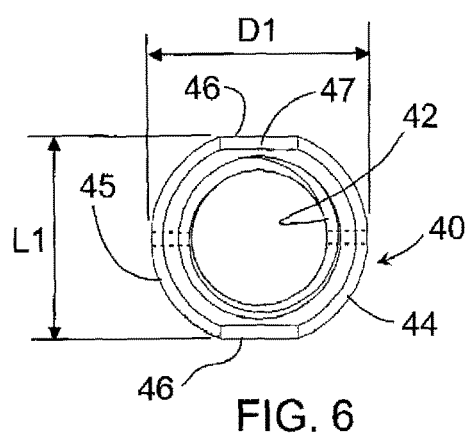
FIG. 6 is a top plan view of a ball insert element of the anchor device shown in FIG. 2.

Of course, a ball element that is too large to pass through the opening 28 cannot be readily inserted into the socket 26. The present invention addresses this matter by a ball insert element 40, illustrated in detail in FIGS. 6-7. The ball insert 40 defines a central threaded bore 42 that is provided for connection to a yoke component 50, as described in more detail herein. The ball insert is generally in the form of a truncated sphere, whereby the outer surface 44 of the ball insert includes a spherical surface 45 that is sized to closely approximate the spherical socket 26, as shown in FIG. 5. Thus, spherical surface 45 defines an outer spherical diameter $D_1$, that is slightly less than the interior diameter of the spherical socket 26, but greater than the diameter of opening 28. As seen more particularly in FIG. 8b, the ball insert 40 is further formed to have a cylindrical portion defined by curved surfaces 46. The curved surfaces 46 of cylindrical portion define an outer diameter $D_2$ about axis A as depicted in FIG. 8b. Axis A in one arrangement is formed to be generally perpendicular to the axis of the central threaded bore 42. In accordance with one aspect of the invention the maximum diameter $D_2$ is slightly less than the planar chordal diameter of socket opening 28 (FIG. 8a) and defines an insert dimension for placing the ball insert 40 into the socket 26 as will be defined. While curved surfaces 46 are preferably formed to define a cylindrical insert dimension $D_2$, it should be appreciated that other configurations may be considered, such as one or more flattened outer surfaces, provided that a maximum insert dimension such as diameter $D_2$ is formed less than the maximum dimension of the socket opening 28.

The benefit of this configuration for the ball insert 40 can be readily appreciated upon consideration of the sequence in FIGS. 8a-8c depicting insertion of the ball insert 40 into the socket 26 of the bone screw 20. As shown in FIG. 8b, the ball insert 40 is rotated at least 90° so that the insert dimension $D_2$ with curved surfaces 46 is aligned to pass through planar chordal opening 28 and into the socket 26. The insert dimension $D_2$ is oriented so that axis A of ball insert 40 is essentially aligned along the axis of the bone screw. The depth of the socket 26 is sufficient to fully receive the rotated ball insert 40 so that the spherical surface 45 exposed in the view of FIG. 8b is within the socket. Then, in the final step shown in FIG. 8c, the ball insert 40 is further rotated at least 90° so that the threaded bore 42 faces upward through the socket opening 28. In this position, the spherical surface 45 of the ball insert is juxtaposed with the interior of the spherical socket 26, as shown in FIG. 5, and the ball insert 40 is captively retained in the socket 26 for swivel movement therewithin.

Figure 7:
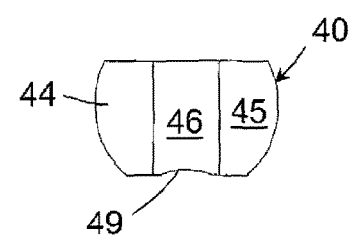
FIG. 7 is a side elevational view of the ball insert shown in FIG. 6.

The ball insert 40 is further provided along axis A as seen in FIG. 8a with a transverse bore 48 that may be aligned with the transverse bore 32 in the spherical head 24 of the bone screw, as shown in FIG. 5 and FIG. 8a. As can be seen from the figures, the ball insert is truncated at the top and bottom of the insert. However, the ball insert in this arrangement is not symmetric—i.e., more of the top of the spherical ball is truncated than the bottom of the ball. Further, as a result of the formation of the curved cylindrical surfaces 46, the lower truncated surface has indentations 49 as illustrated in FIG. 7. When the ball 40 is rotated as depicted in FIG. 8b, the indentations 49 may be directed toward the bottom of socket 26 and are not visible through the socket opening.

Returning to FIGS. 4-5, the anchor device 15 further includes a yoke 50 having a threaded stem 52 configured to engage the threaded bore 42 in the ball insert 40. The stem is provided with a shoulder 53 that preferably abuts the ball insert 40 when the stem 52 is fully threaded into the bore 42 of the insert. The yoke 50 includes yoke arms 54a, 54b that define a yoke channel 55 therebetween. The gap between the arms 54a, 54b, and consequently the width of the channel, is sized to closely fit the spinal rod 12, as best seen in FIG. 5. The arms 54a, 54b define internal threads 56 at the upper open end of the yoke 50 for engaging a set screw 80, as described below. A bore 57 passes through the threaded stem 52 that is aligned with the bore 30 in the bone screw when the yoke is mounted on the ball insert.

Figure 9:
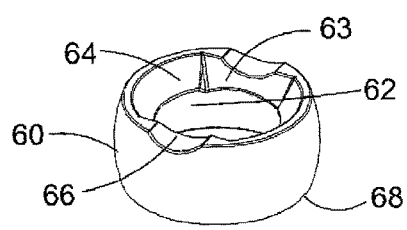
FIG. 9 is a top perspective view of a sleeve component of the anchor device shown in FIG. 2.
Figure 10:
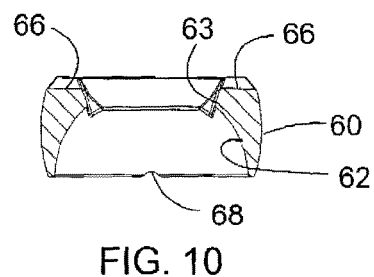
FIG. 10 is a side cross-sectional view of the sleeve shown in FIG. 9.

As shown in FIGS. 8d-8e, a sleeve 60 is interposed between the yoke 50 and the head 24 of the bone screw 20. As further shown in FIGS. 9 and 10, the sleeve 60 defines a lower cavity 62 that has a spherical configuration to substantially match the spherical outer surface 34 of the screw head 24. Sleeve 60 sits on the outer surface 34 for sliding movement thereon, and serves as a clamping element for the rod 12 relative to the yoke as will be described. The sleeve further defines an upper cavity 64 that generally parallels the outer surface of the yoke arms 54a, 54b, as seen in FIG. 5. The upper face of the sleeve 60 defines opposite rod grooves 66 sized to receive the spinal rod 12 therein. The lower face of the sleeve defines opposite notches 68 that are oriented 90° from the rod grooves 66. The notches 68 are arranged to align with the transverse bores 32 and 48 when the anchor device is assembled. The notches and bores are sized to receive retaining pins 155 (FIG. 11) as described in more detail herein. In a preferred arrangement, sleeve 60, is provided with opposing recessed surfaces 63 that engage the arms 54a, 54b of the yoke 50 to key the sleeve 60 to yoke 50 in a manner that allows common swivel movement of the yoke 50 and sleeve 60 relative to the screw head 24.

Figure 11:
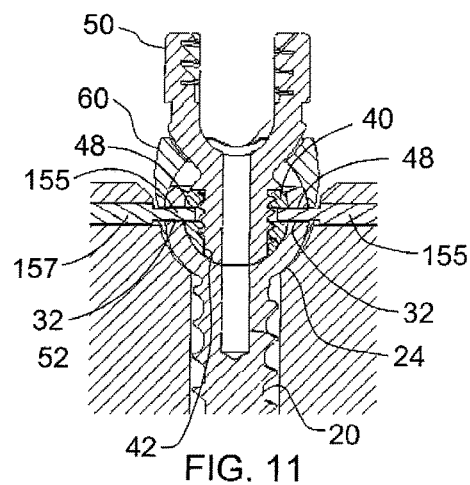
FIG. 11 is a longitudinal cross-sectional view of a fixture with holding pins for holding the position of the ball insert relative to the socket during engagement of the yoke.

As depicted in FIG. 8d-8e, after the ball insert 40 is properly aligned and captively retained as shown in FIG. 8c, the yoke 50 may engage the insert 40 to form an assembly therewith. In accordance with the preferred manner of assembly of the anchor device 15, the threaded stem 52 of the yoke is extended through the sleeve 60 with the sleeve keying surfaces 63 aligned with the yoke arms 54a, 54b. The threaded stem 52 is then threaded into engagement with the threaded bore 42 of the ball insert. In order to achieve this threaded engagement it is necessary to hold the ball insert 40 as the stem 52 of the yoke is threaded into the bore 42. Thus, in one aspect of the invention, the ball insert 40 is oriented within the spherical socket 26 so that the transverse bores 48 in the insert are aligned with the transverse bores 32 in the screw head. When the bores are aligned, pins 155 may be pushed therethrough, taking care that the pins do not extend into the threaded bore 42, as illustrated in FIG. 11. Arms 157 of a forceps-like tool may be used to introduce the pins into the bores.

With the pins 155 in position, the sleeve 60 may be placed over the head of the bone screw with the notches 68 aligned with the pins 155. The yoke is then extended through the sleeve with the stem engaging the threaded bore 42 of the ball insert. The pins 155 resist rotation of the ball insert 40 as the stem is threaded into the bore. The yoke 50 is threaded into the ball insert until the shoulder 53 contacts the upper face of the ball insert 40 as shown in FIGS. 4-5.

Figure 12:
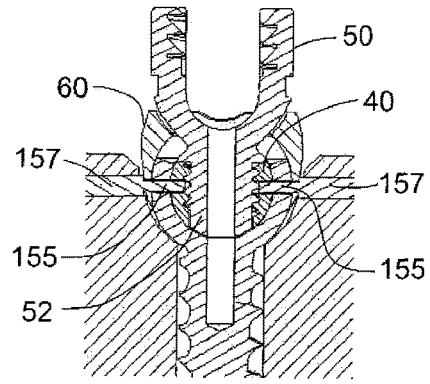
FIG. 12 is a longitudinal cross-sectional view of the fixture with holding pins used to crimp or swage the threads of the yoke to fix the yoke to the ball insert.

In an additional feature, the pins 155 may be used to crimp, swage or deform the threads of the stem 52 of the yoke 50. Thus, the tool arms 157 may be pressed toward each other so that the pins 155 contact the threaded stem 52, as shown in FIG. 12. When the threads are distorted the stem 52 of the yoke cannot back out or unthread from the ball insert 40. Once the yoke and ball insert have been locked together, the pins 155 can be removed. It is understood that this initial assembly of the anchor device, namely the steps shown in FIGS. 8a-8e, occur prior to introduction of the anchor device 15 into the spine, preferably by the supplier. It can also be appreciated that once the yoke 50 is locked with ball insert 40, the ball insert 40 is free to swivel within the fastener socket 26 allowing the yoke attached thereto to freely angulate in multiple directions. Since sleeve 60 is keyed to yoke 50 it likewise freely slides on outer surface 34 of fastener head 24 as the yoke 50 moves, until the anchor device components are locked in use. Furthermore, even though the ball insert 40 is free to swivel within socket 26, once the yoke 50 is attached the insert 40 remains captively retained since the insert 40 will not be able to move to a position where its insert dimension $L_1$ is aligned with the socket opening 28.

Figure 13:
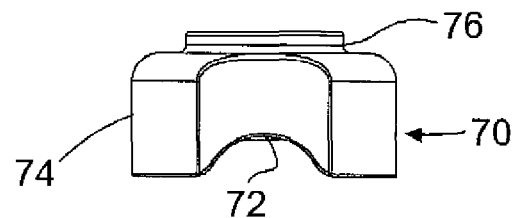
FIG. 13 is a longitudinal elevational view of a cap with set screw of the anchor device of FIG. 2.
Figure 14:
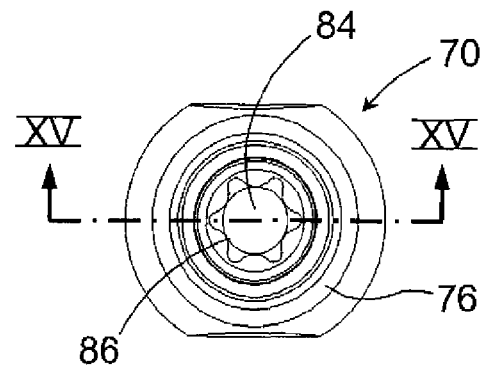
FIG. 14 is a top plan view of the cap shown in FIG. 13.

Returning again to FIGS. 4-5, the assembly of the rod 12 to the fastener 20 is shown. The rod 12 is initially placed between the arms of the yoke 50 to rest on the rod grooves 66 of the sleeve 60. The yoke channel 55 may then be closed, securing the rod within. In accordance with a further feature of the invention, a cap 70 is fitted over the top of the yoke arms 54a, 54b. The cap 70 as further detailed in FIGS. 13-15, includes a generally cylindrical skirt 74 that fits snugly around the arms 54a, 54b to prevent the arms from splaying outward as set screw 80 is threaded into the arms. The skirt 74 is preferably provided with diametrically opposed flats 75 that correspond to the transverse opening of the yoke channel 55, as best seen in FIG. 8f. The flats 75 define rod grooves 72 that align with, but do not contact, the rod 12 when it is situated within the yoke channel 55.

Figure 15:
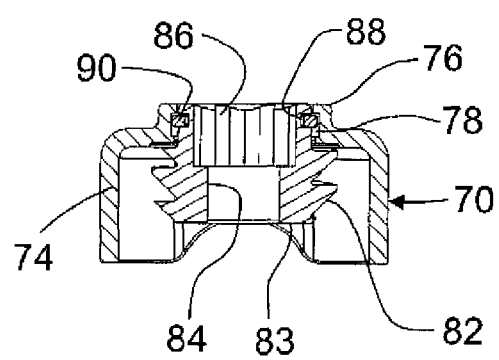
FIG. 15 is a cross-sectional view of the cap of FIG. 14 taken along viewing line XV-XV.

The cap 70 includes an upper boss 76 that defines an enlarged circumferential interior groove 78. This groove is sized to receive a retaining ring or snap ring 90 therein, as seen in FIG. 5 and FIG. 15. The groove is axially enlarged or lengthened so that the snap ring 90 may translate up and down within the boss 76 for reasons explained below.

The set screw 80 is provided with a threaded stem 82 that is configured to engage the internal threads 56 of the yoke arms 54a, 54b. Preferably the threaded engagement between set screw and yoke are in the form of buttress threads, as depicted in FIGS. 4-5. The buttress threads minimize the outward force produced as the set screw is threaded into the yoke. Thus, the use of buttress threads help minimize any splaying of the yoke arms that might otherwise occur when the set screw 80 is threaded tightly into the yoke 50. In addition as shown in FIG. 15, the bottom of the set screw is recessed upwardly of the bottom of the skirt 74 of cap 70. Thus, when cap 70 is placed over the arms 54a, 54b of yoke 50, not only does the close fit of the skirt 74 relative thereto prevent splaying as noted, but skirt 74 also serves as a guide to align the threads 82 of set screw 80 into the threads 56 of the yoke 50, thereby also reducing the risk of disadvantageous cross-threading.

The set screw 80 includes a pressure face 83 that contacts and exerts a securing force against the spinal rod 12. The pressure face 83 as well as the rod surface may exhibit surface features intended to enhance the fixation between set screw and rod, as is known in the art. In particular, a surface roughness may be provided that becomes deformed or cold formed when the set screw is tightened onto the rod. This feature helps prevent the rod from slipping axially (along its length) within the anchor device 15.

The set screw 80 defines a bore 84 therethrough. The upper portion 86 of the bore may be configured to receive a driving tool, such as with hex or TORX surfaces.

Like the cap 70, the set screw 80 defines a circumferential groove 88 (FIG. 4) configured to receive the retaining ring 90 therein. However, unlike the cap groove 78, the groove 88 in the set screw is preferably sized to closely fit the snap ring. Thus, while the snap ring 90 is held by the set screw, the snap ring is free to translate within the elongated cap groove 78. The elongated groove 78 is thus intended to allow the set screw 80 to fully engage the rod 12 while the cap 70 essentially floats by virtue of the snap ring 90 translating within groove 78. Thus, the cap 70 effectively exerts no force on the rod 12 or on the top surface of the yoke 50, even if some contact is made.

Figure 16:
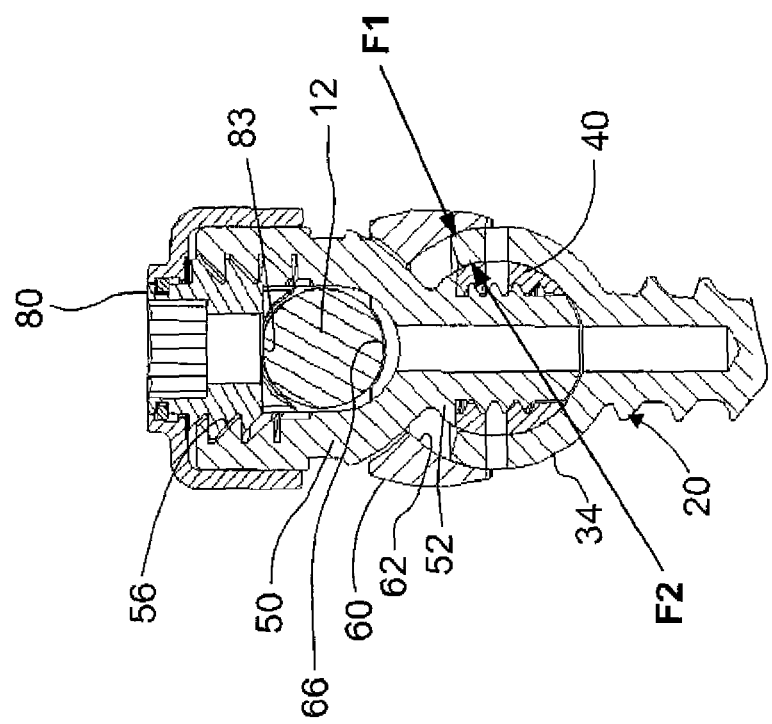
FIG. 16 is a longitudinal cross-sectional view similar to FIG. 5 showing forces generated to lock the components of the anchor device of FIG. 2.

The set screw 80 generates the force that locks the ball insert 40 within the spherical socket 26 at the desired angular orientation, and that further locks the spinal rod 12 within the anchor device 15. In particular, once the anchor device 15 has been fully assembled about the rod 12, as best seen in FIG. 16, the set screw 80 is tightened within the yoke 50. As the screw is tightened, it presses against the rod 12, clamping it between the pressure face 83 of the set screw and the rod grooves 66 in the sleeve 60. As the set screw is driven further into the internal threads 56 of the yoke 50, the set screw pushes the rod 12 downwardly until the lower cavity 62 of the sleeve 60 is firmly engaged to the outer surface 34 of the head 24 of the bone screw generating locking force, F1.

At this point the sleeve 60 and rod 12 can move no further toward the bone screw 20. Therefore, any further tightening of the set screw is reacted by the yoke itself. As the set screw is driven further into the yoke internal threads (i.e., advancing toward the head of the bone screw) this reaction force pulls the yoke upward. While the yoke is pulled upward with continued rotation of the set screw, the stem 52 of the yoke pulls the ball insert 40 upward, owing to the fixed engagement between the yoke stem and the ball insert. As the ball insert is pulled upward, it bears forcefully against the upper face of the spherical socket 26, with a force F2 clamping the socket wall between the sleeve 60 and the ball insert 40 and thereby locking the ball insert 40 and yoke 50 relative to fastener 20. Any tendency of the socket 26 to attempt to gap at the socket opening 28 is resisted by the sleeve 60 that is already in firm engagement about the outer surface 34 of the screw head.

It can thus be appreciated that the entire anchor device can be adjustably secured in a fixed relationship simply by rotation of the set screw 80. As the set screw is threaded into the yoke threads it ensures solid clamping of the bone screw head 24 between the lower cavity 62 of the sleeve 60 and the spherical surface 45 of the ball insert 40, regardless of the angular orientation of the yoke and rod relative to the screw. The rod itself is firmly clamped between the set screw and the lower sleeve. It can further be appreciated that the entire anchor device may be tightened by simply tightening the set screw.

Figure 17:
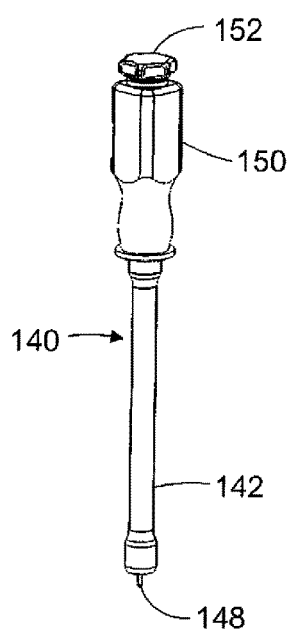
FIG. 17 is a side elevational view of a fastener inserter tool for use with one embodiment of the anchor device of the present invention.
Figure 18:
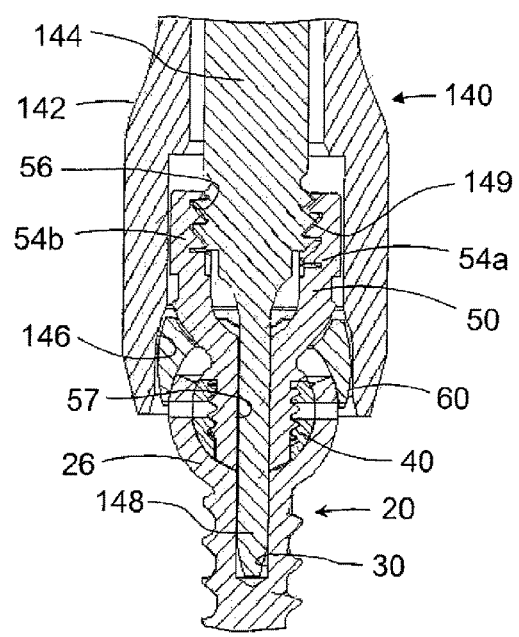
FIG. 18 is a longitudinal cross-sectional view of the fastener inserter tool shown in FIG. 17 engaged to components of the anchor device of FIG. 2.

In use, the bone screw and sleeve assembly of FIG. 8e is provided together with one or more suitably sized rods 12 and a cap 70 so that a spinal fixation system 10 may be implanted into a patient. The surgeon may insert the bone screw assembly with a suitable screw inserter 140 as shown, for example, in FIGS. 17-18. The screw inserter 140 includes an outer sleeve 142 and an inner shaft 144 rotatably disposed within the sleeve. As shown in the view of FIG. 18, the end 146 of the outer sleeve 142 is configured to contact the proximal upper surface of the sleeve 60. The outer sleeve 142 is fixed to a handle 150, while the inner shaft is fastened to a tightening knob 152 that is rotatably supported on the handle. The inner shaft 144 includes a pin end 148 that is sized to extend through the bore 57 in the yoke 50 and into the bore 30 at the base of the spherical socket 26. The pin end 148 ensures co-axial alignment of the driving tool 140 and the bone screw threaded shank 22. The inner shaft further includes intermediate threads 149 axially offset from the pin end 148. These threads 149 are arranged to engage the internal threads 56 of the yoke arms 54a, 54b.

The threads 149 on the inner shaft 144 of the tool 140 operate similar to the set screw 80. Specifically, as the threads are driven into the internal threads 56 of the yoke 50, the pin end 148 reacts against the bottom of the bore 30 in the bone screw to generate an upward force on the yoke 50. As the yoke is pushed upward, it pulls the ball insert 40 with it, thereby driving the insert into the spherical socket. When the inner shaft 144 has been fully tightened, the screw inserter tool 140, yoke 50, ball insert 40 and bone screw 20 form a rigid connection. The handle 150 of the outer sleeve 142 may then be used to drive the bone screw into the vertebral bone, either manually or with the assistance of an additional driving tool after a suitable hole has been drilled in the pedicle of a vertebra.

Once the bone screw 20 is threaded in position into the spine, the next step to completing the fixation system, such as system 10 shown in FIG. 1, is to introduce the rod 12 into the yoke 50 of the anchor device 15. The rod may be contoured to match the normal curvature of the spine, either in lordosis or kyphosis depending upon the instrumented vertebral level. In some cases, the spine exhibits a lateral curvature, such as scoliosis, that is preferably corrected, at least partially, by the fixation system 10. Thus, in certain cases, the rod 12 itself may be laterally offset from the position of the bone screw engaged within the underlying vertebra. In these cases, the variable angle capabilities of the anchor device of the present invention come into play.

Figure 19:
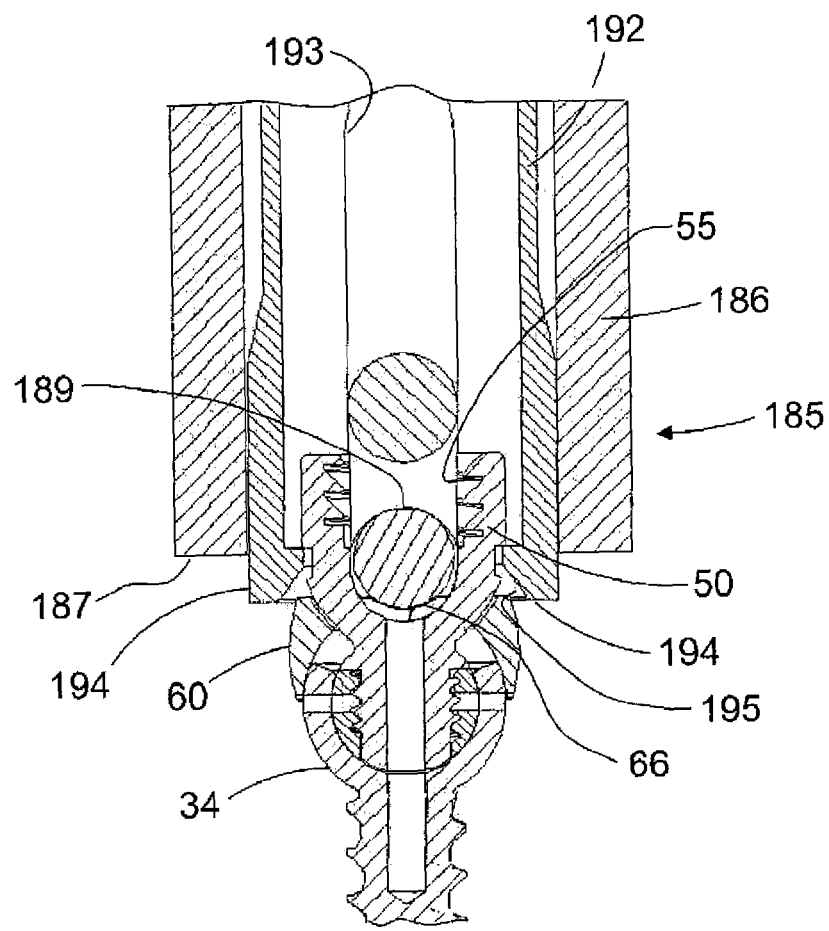
FIG. 19 is a longitudinal cross-sectional view of the lower end of a rod persuader tool engaged to a partially assembled anchor device of FIG. 2.

To accomplish the introduction of the rod 12 into the yoke channel 55 of the yoke 50, a rod persuader tool 185 is provided, as shown in FIG. 19. The rod persuader tool 185 includes an outer tube 186 and an inner tube 192 concentrically disposed within the outer tube for relative axial movement. The outer tube 186 defines a rod notch 189 at its bottom end 187. The inner tube 192 defines a slot 193 that forms legs 194 at the distal end. The legs define an inner shoulder 195 that is configured to suitably engage the partially assembled anchor device. The inner shoulders 195 may engage a groove (not shown) in the outer surface 34 of fastener socket 26. In another embodiment, the yoke 50 may be modified to have a groove (not shown) that may be engaged by the inner shoulders 195. In either embodiment, the legs 194 are configured to partially encircle and firmly grasp the partially assembled anchor device, while the slot 193 accommodates the initial presence of the rod 12 within the yoke channel 55. A guide pin 190 spans the diameter of the outer tube 186 and fits within the slot 193 to control the relative axial movement between the outer tube 186 and the inner tube 192. A suitable mechanism is provided to move the outer tube 186 downward axially relative to inner tube 192. As the outer tube 186 moves downward, it forces the rod 12 into the yoke channel 55 by lower notch 189 and into the rod groove 66 of the sleeve 60.

With the rod 12 suitably placed into the yoke 50, the spinal fixation device 10 may then be completed. Cap 70 as shown in FIG. 8f is then assembled to the yoke 50, as described above with reference to FIGS. 4-5, to lock the rod 12 relative to the yoke 50 and the yoke 50 relative to the bone fastener 20. It should be appreciated that the spinal fixation device 10 as particularly described herein has the advantage of establishing a low profile, since the outer surface of the screw head 24 may be driven down relatively deeply into the pedicle of the vertebra, while still maintaining swivel movement of the yoke 50 until the set screw 80 is tightened. Furthermore, the relatively large surface area of spherical surface 45 of the ball insert 40 tightly pressed against the interior surface of the screw socket 26 provides for a very rigid construct for locking the polyaxial motion of the yoke 50 relative to the screw 20.

Figure 20:
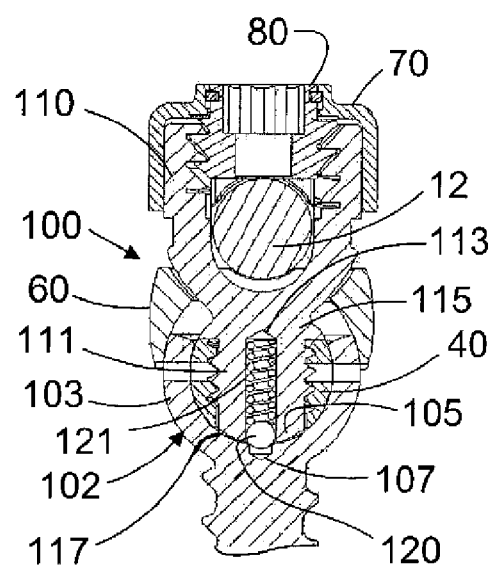
FIG. 20 is a longitudinal cross-sectional view of an anchor device according to an alternative embodiment of the invention.

Another embodiment of the invention, illustrated in FIG. 20, provides an anchor device 100 having a bone engaging fastener 102 with a spherical head 103. The head defines a spherical socket 105 like the bone screw 20 described above. The ball insert 40, lower sleeve 60, upper sleeve 70 and set screw 80 may be constructed as described above. The yoke 110 includes a threaded stem 111 and a shoulder 115 for threaded engagement with the ball insert. However, unlike the previously described yoke 50, the yoke 110 includes an internal cavity 113 extending from the distal end 117. This cavity corresponds to a dimple 107 formed in the base of the spherical socket 105.

In accordance with this embodiment, a retention ball 120 is seated within the dimple and residing within the cavity 113. A spring 121 is disposed within the cavity to exert a relatively slight force against the ball 120. The ball and dimple serve as a releasable detent to maintain a predetermined orientation between the ball insert 40 and the screw head 103 for ease of screw insertion. The spring maintains pressure on the seating ball 120 and also exerts an upward force on the ball insert 40 to help engage the insert within the spherical socket 105 of the bone screw head. The fixation of the anchor device 100 otherwise proceeds as outlined above by tightening the set screw 80.

Figure 21:
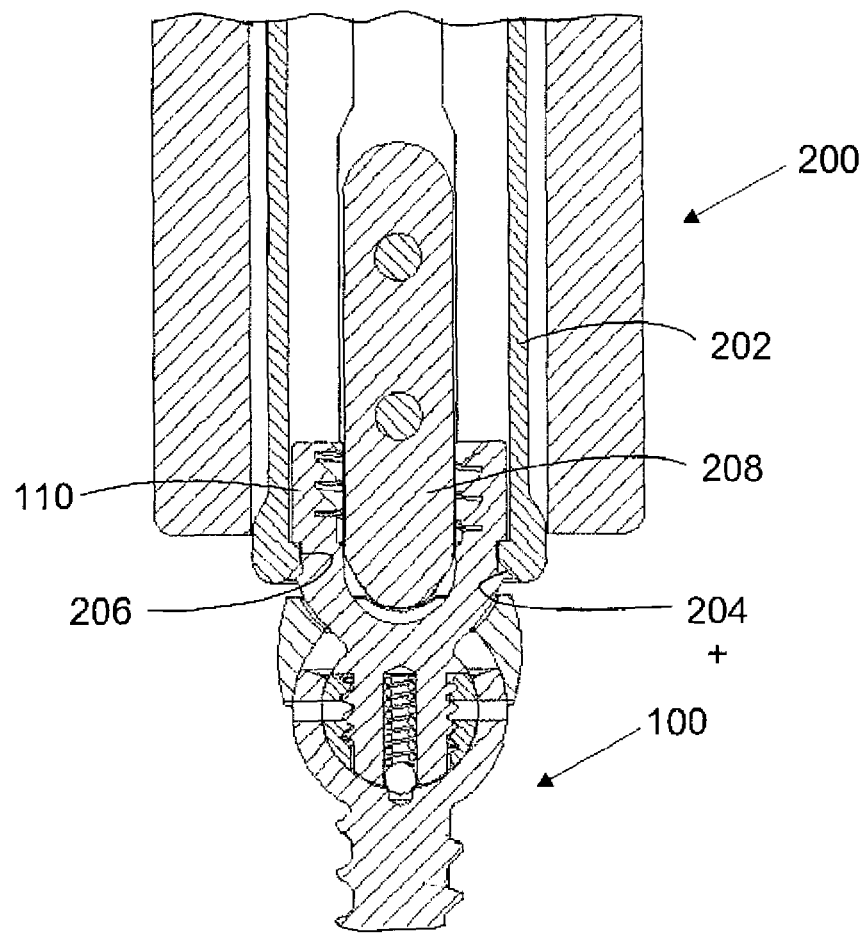
FIG. 21 is a longitudinal cross-sectional view of a screw inserter tool engaged to a partially assembled anchor device, such as the alternative anchor device shown in FIG. 20.

A suitable insertion tool 200 for inserting device 100 into a vertebra is shown in FIG. 21. Tool 200 has an inner tube 202 with shoulders 204 partially configured to engage a groove 206 formed in the outer surface of yoke 110. Tool 200 further has a driver element 208 that is configured to fit within the channel of yoke 110 to thread the device 100 into a vertebra.

As such, by virtue of the discrete positioning of the retention ball 120 in the dimple 107, one advantage of the anchor device 100 is the feature of releasably holding the yoke 110 in axial alignment with the longitudinal axis of fastener 102. Such an advantage is useful, as described with reference to FIG. 21, in attaching the driving tool 200 to the yoke 100. With the yoke 100 aligned axially with the fastener 102, driving the fastener threads into the pedicle is readily facilitated. In a particular arrangement, the spring 121, which is shown in one form in FIG. 21 as a helical spring, provides a spring force on the order of 1.0-2.0 lbs/inch.

It should also be appreciated that in addition to providing the discrete releasable detent when ball 120 is seated in dimple 107 or other suitable recess, further advantage is provided when the ball 120 is not seated in dimple 107. In such disposition, as noted above, because the spring 121 maintains pressure on the ball 120, an upward force is applied pushing the ball insert 40 upwardly against the inner surface of the spherical socket 105 of the fastener 102. Such a force not only provides sufficient friction to allow the yoke 110 and the outer sleeve 60 to slidably articulate about the spherical socket 105, but to be movably held in place by the friction. Thus, the yoke 110 can be oriented to various positions and will stay in place to receive a rod 12, for example, that may be bent to adapt to the particular curvature of the spine.

It should also be understood that while a helical spring 121 is shown and described, other spring members may be used. For example, a resilient polymer that is compressible within cavity 113 of yoke 110 may be used. In addition, while one dimple 107 in spherical socket 105 is shown, additional dimples may be provided to allow for multiple discrete releasable detents, if desired. Also, in certain instances, the spring 121 or other spring or friction member may be used to produce friction in the absence of the dimple 107 so as to allow frictional movement of the yoke 110 relative to the fastener 102 without a discrete retention stop.

Figure 22:
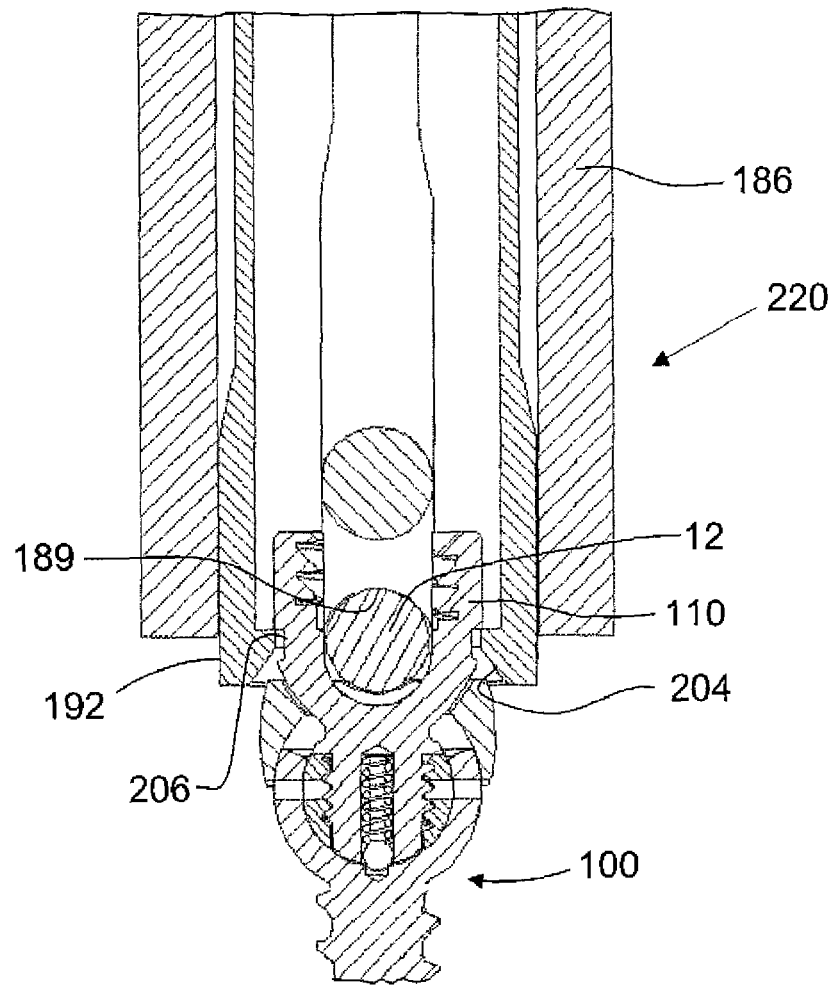
FIG. 22 is a longitudinal side cross-sectional view of the lower end of the rod persuader tool engaged to a partially assembled modified anchor device, such as the alternative device shown in FIG. 20.

A rod persuader tool 220 for particular use with device 100 is shown in FIG. 22. Tool 220 is similar to the rod persuader 185 having an outer tube 186 axially movable with respect to an inner tube 192. The shoulders 204 are configured to engage yoke groove 206 and hold the device 100 while an elongated rod 12 is pushed into the yoke 110 of the device 100. The rod is pushed by notch 189 upon downward movement of outer tube 186. Completion of the spinal fixation system takes place by assembly of the cap 70 over the yoke 110 and tightening of the set screw 80 against the rod 12 as described above.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A bone screw for anchoring an elongate connecting rod to a vertebra of a spine comprising:
    a fastener having a bone engaging portion and a head having an outer surface and a lower portion having a bone engaging surface;
    a yoke having at one end a rod receiving channel for receiving an elongate connecting rod and an opposite end configured to couple to said fastener for articulating movement therewith;
    a ball and socket joint articulatingly coupling said yoke and said head of said fastener comprising a ball including an outer surface having alternating spherical and cylindrical portions, said spherical portion having a diameter, said cylindrical portion intersecting said spherical portion at said spherical portion diameter, said ball being captively retained within said socket for articulation therewithin in a manner to allow said yoke to swivel relative to said fastener.

2. The bone screw of claim 1, wherein said socket is a spherical socket defining an interior spherical diameter and having a socket opening defining a chordal diameter, and wherein said spherical portion of said ball has a spherical diameter that is less than said interior spherical diameter of said socket but greater than said chordal diameter, and wherein said cylindrical portion of said ball has a cylindrical diameter that is less than said chordal diameter of said socket opening.

3. The bone screw of claim 2, wherein said ball of said ball and socket joint is attached to said opposite end of said yoke for common articulating movement with said yoke.

4. The bone screw of claim 3, wherein said spherical socket is formed within the head of said fastener.

5. The bone screw of claim 2, further comprising a fastening element supported by said yoke for securing said elongate connecting rod to said yoke while locking said yoke relative to said fastener.

6. The bone screw of claim 5, wherein said yoke channel defines internal threads; and, wherein said fastening element includes a set screw configured for threaded engagement with said internal threads of said yoke channel.

7. The bone screw of claim 6, wherein said set screw includes buttress threads.

8. In a bone screw for anchoring an elongated rod to the spine of the type comprising a fastener having a bone engaging portion and a head having an outer surface, and a yoke having a rod receiving channel and supported by the head of said fastener for swiveling movement, an improvement comprising:
    a ball and socket joint articulatingly coupling said yoke and the head of said fastener comprising a ball including an outer surface having alternating spherical and cylindrical portions, said cylindrical portion defining a cylinder axis, said ball being captively retained within said socket for articulation therewithin in a manner to allow said yoke to swivel relative to said fastener,
    said ball and socket being attached by a process of initially inserting said cylindrical portion of said ball into said socket in a first orientation and then rotating said ball to a second orientation to captively retain said ball within said socket.

9. The improvement of claim 8, wherein said socket is a spherical socket having a spherical diameter and an opening, said opening defining an opening axis and a planar chordal diameter less than said spherical diameter.

10. The improvement of claim 9, wherein said spherical portion of sad ball has a spherical diameter greater than said chordal diameter and less than the spherical diameter of said socket, and wherein said cylindrical portion of said ball has a cylindrical diameter that is less than said chordal diameter of said socket opening.

11. The improvement of claim 10, wherein said cylinder axis of said cylindrical portion defines an insert direction and said spherical diameter of the spherical portion of said ball defines a captive dimension, and wherein the process of initially inserting said cylindrical portion of said ball into said socket in a first orientation comprises the steps of placing said ball into said socket through said socket opening in said insert direction along said opening axis.

12. The improvement of claim 11, wherein the process of rotating said ball to a second orientation to captively retain said ball within said socket comprises rotating said cylindrical portion such that said cylinder axis is transverse to said opening axis of said socket.

* * * * *